US00PP26280P3

(12) United States Plant Patent

Klemm et al.

(10) Patent No.: US PP26,280 P3

(45) Date of Patent: Dec. 29, 2015

(54) *PELARGONIUM* PLANT NAMED 'KLEIZ13366'

(50) Latin Name: ***Pelargonium* sp.**
Varietal Denomination: KLEIZ13366

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 253 days.

(21) Appl. No.: 13/998,695

(22) Filed: Nov. 25, 2013

(65) Prior Publication Data

US 2015/0150172 P1 May 28, 2015

(51) Int. Cl.
*A01H 5/02* (2006.01)

(52) U.S. Cl.
USPC ..... Plt./330

(58) Field of Classification Search
USPC ..... Plt./324, 325, 330
See application file for complete search history.

*Primary Examiner* — Susan McCormick Ewoldt
*Assistant Examiner* — Karen Redden
(74) *Attorney, Agent, or Firm* — Barbara Campbell; Bethany R. Roahrig; Cochran Freund & Young, LLC

(57) ABSTRACT

A new *Pelargonium* plant particularly distinguished by having shiny red flowers, a medium growth habit and rich flowering, and is very early to flower, is disclosed.

1 Drawing Sheet

Genus and species: *Pelargonium* sp.
Variety denomination: 'KLEIZ13366'.

BACKGROUND OF THE NEW PLANT

The present invention comprises a new and distinct variety of *Pelargonium*, botanically known as *Pelargonium* sp. and hereinafter referred to by the variety name 'KLEIZ13366'. 'KLEIZ13366' originated from a controlled-cross between the proprietary female *Pelargonium* variety 'PP 06 086' (unpatented), having orange flowers, and the male *Pelargonium* variety 'Fernando' (patent status unknown), having blue-red flowers.

In June 2008 the two *Pelargonium* parental lines 'PP 06 086' and 'Fernando' were crossed in Stuttgart, Germany and seeds were obtained. The seeds were sown and plants were grown for evaluation. A plant line was selected in June 2009 and named 'KLEIZ13366'. In June 2009 'KLEIZ13366' was first vegetatively propagated by vegetative cuttings. 'KLEIZ13366' was found to reproduce true to type in successive generations of asexual propagation via vegetative cuttings in Stuttgart, Germany.

CROSS REFERENCE TO RELATED APPLICATIONS

Plant Breeder's Rights for 'KLEIZ13366' were applied for in Canada on Feb. 8, 2013, Application No. 13-7925. 'KLEIZ13366' has not been made publicly available or sold more than one year prior to the filing date of this application.

SUMMARY

The following are the most outstanding and distinguishing characteristics of this new variety when grown under normal horticultural practices in Stuttgart, Germany.

1. Shiny red flowers;
2. A medium growth habit and rich flowering; and
3. Is very early to flower.

DESCRIPTION OF THE PHOTOGRAPH

This new *Pelargonium* plant is illustrated by the accompanying photograph which shows an overall view of the plant.

The photograph is of a 4 to 5-month-old plant grown in Stuttgart, Germany under greenhouse conditions in May 2012.

The colors shown are as true as can be reasonably obtained by conventional photographic procedures.

DESCRIPTION OF THE NEW VARIETY

The following detailed descriptions set forth the distinctive characteristics of 'KLEIZ13366'. The data which define these characteristics were collected from asexual reproductions carried out in Stuttgart, Germany. Data was collected on 15-week-old plants grown in an indoor trial in Stuttgart, Germany under greenhouse conditions in April 2013. Color references are to The R.H.S. Colour Chart of The Royal Horticultural Society of London (R.H.S.), $5^{th}$ edition (2007).

Classification:
- *Family*.—Geraniaceae.
- *Botanical*.—*Pelargonium* sp.
- *Common*.—*Pelargonium*.
- *Designation*.—'KLEIZ13366'.

Parentage:
- *Female parent*.—*Pelargonium* line 'PP 06 086' (unpatented).
- *Male parent*.—*Pelargonium* line 'Fernando' (unpatented).

Plant:
- *Habit*.—Upright.
- *Height*.—20.0 cm.
- *Spread*.—28.0 cm.
- *Life cycle*.—Annual, greenhouse January to April and outside May to October.
- *Form*.—Rounded, potted plant.

*Time to produce a rooted cutting.*—18 days.
*Time to bloom from propagation.*—77 days.
*Lastingness of inflorescence on the plant.*—About 2 weeks.

Stems:
*Color.*—RHS 137B.
*Pubescence.*—Present.
*Stem form.*—Round.
*Diameter.*—0.8 cm.
*Length.*—12.0 cm to 14.0 cm.
*Internode length.*—2.0 cm.
*Anthocyanin.*—Absent.

Leaves:
*Arrangement.*—Alternate.
*Shape.*—Ivy shaped.
*Apex.*—Obtuse.
*Base.*—Open.
*Margin.*—Crenate.
*Surface texture.*—Upper surface: Rough. Lower surface: Smooth.
*Length.*—6.0 cm.
*Width.*—7.0 cm.
*Color.*—Upper surface: RHS 147A. Zone: RHS 177C. Lower surface: RHS 147B.
*Surface pubescence.*—Upper surface: Sparse. Lower surface: Absent.
*Petiole.*—Length: 6.0 cm to 8.0 cm. Color: RHS 137C.
*Venation pattern.*—Palmate.
*Venation color.*—Upper surface: RHS 137A. Lower surface: RHS 137D.

Inflorescence:
*Umbels.*—Length: 5.0 cm to 6.0 cm. Diameter: 6.0 cm.
*Individual florets of the umbel.*—Depth: 1.5 cm. Diameter: 3.0 cm.
*Fragrance.*—Absent.

Flower buds:
*Cluster shape.*—Round.
*Cluster size.*—Length: 2.0 cm. Width: 2.0 cm.
*Texture.*—Rough.
*Bud.*—Shape: Elliptic to ovate. Apex: Cuspidate. Base: Obtuse. Margin: Smooth. Color: RHS 147A.

Petals:
*Quantity per flower.*—5 to 8.
*Shape.*—Ovate.
*Apex.*—Smooth, round.
*Base.*—Obtuse.
*Margin.*—Entire.
*Length.*—2.0 cm.
*Width.*—1.5 cm.
*Color of lobes.*—Upper and lower lobes: Upper surface: RHS 45B. Lower surface: RHS 45D.

Sepals:
*Number per flower.*—5.
*Shape.*—Elliptic to ovate.
*Apex.*—Acute.
*Base.*—Obtuse.
*Margin.*—Entire.
*Color.*—Upper surface: RHS 137A. Lower surface: RHS 137D.
*Length.*—0.7 cm.
*Width.*—0.5 cm.

Pedicel:
*Length.*—0.5 cm to 1.3 cm.
*Diameter.*—0.15 cm.
*Color.*—RHS 179B and RHS 137C; RHS 137C is predominant and beginning at the bottom; RHS 179B is more on the top in spring and summertime, later (winter) very less.

Peduncle:
*Length.*—10.0 cm to 15.0 cm.
*Diameter.*—0.6 cm.
*Color.*—RHS 180D and RHS 137D; RHS 137D is mostly very predominant beginning from the bottom; the last part on the top is RHS 180, but very less and not in the winter.
*Texture.*—Rough.

Reproductive organs:
*Stamens.*—Anther length: 0.2 cm. Filament length: 0.6 cm. Filament color: RHS 48D. Pollen amount: Moderate. Pollen color: RHS 32C.
*Pistils.*—Number: 1. Stigma color: RHS 59D. Style length: 0.1 cm. Style color: RHS 56D. Ovary arrangement: Erect.

Fruit and seed set: None observed.
Disease and pest/insect resistance: None observed.

COMPARISON WITH PARENTAL LINES AND KNOWN VARIETY

'KLEIZ13366' is a distinct variety of *Pelargonium* shiny red flowers, a medium growth habit and rich flowering, and is very early to flower. 'KLEIZ13366' is distinguished from its parents as described in Table 1:

TABLE 1

Comparison with Parental Lines

| Trait | 'KLEIZ13366' | Female parent 'PP 06 086' | Male Parent 'Fernando' |
|---|---|---|---|
| Flower color | Shiny red | Orange | Blue-red |
| Growth | Medium | Small | Compact |
| Earliness of flowering | Very early | Very early | Medium early |

'KLEIZ13366' is most similar to the commercial *Pelargonium* plant named 'Fernando' (patent status unknown). Differences between the two varieties are described in Table 2:

TABLE 2

Comparison with Similar Variety

| Trait | 'KLEIZ13366' | Commercial line 'Fernando' |
|---|---|---|
| Earliness | Very early | Medium early |
| Flower habit | Rich flowering | Medium |
| Flower color | Shiny red | Blue-red |

We claim:

1. A new and distinct variety of *Pelargonium* plant named 'KLEIZ13366' as shown and described herein.

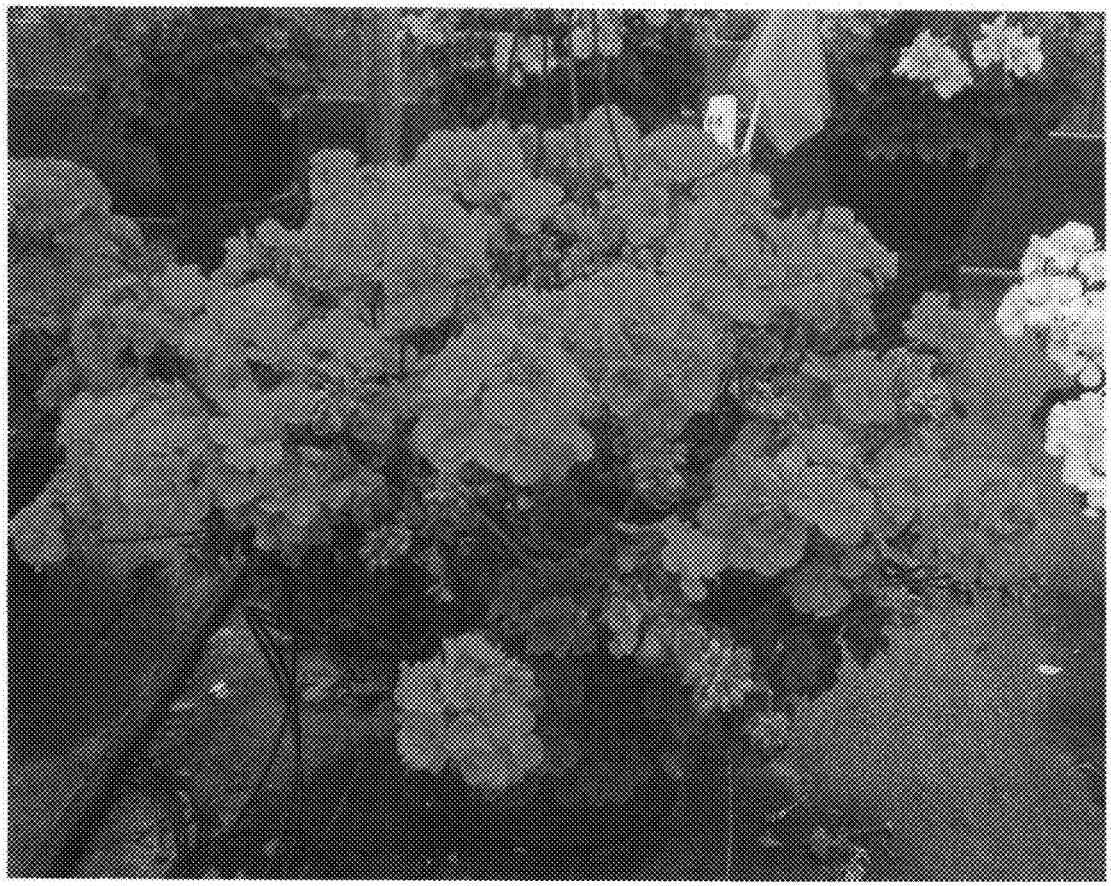

* * * * *